United States Patent [19]

De Lombaert

[11] Patent Number: 5,250,522
[45] Date of Patent: Oct. 5, 1993

[54] PHOSPHONO/BIARYL SUBSTITUTED AMINO ACID DERIVATIVES

[75] Inventor: Stéphane De Lombaert, Bernardsville, N.J.

[73] Assignee: Ciba-Geigy Corporation, Ardsley, N.Y.

[21] Appl. No.: 959,000

[22] Filed: Oct. 9, 1992

[51] Int. Cl.$^5$ .................. A61K 31/66; C07F 9/38; C07F 9/40

[52] U.S. Cl. .................. 514/114; 514/79; 514/85; 514/89; 514/90; 514/91; 514/95; 514/99; 540/542; 544/157; 544/337; 546/22; 548/413; 549/6; 549/218; 558/169; 562/17

[58] Field of Search .............. 558/169; 514/114; 560/38; 562/17

[56] References Cited

U.S. PATENT DOCUMENTS

| | | | |
|---|---|---|---|
| 4,721,726 | 1/1988 | Berger | 514/464 |
| 4,939,261 | 7/1990 | Ksander | 514/357 |
| 4,963,539 | 10/1990 | Delaney | 514/119 |
| 5,021,430 | 6/1991 | Ksander | 514/332 |
| 5,061,806 | 10/1991 | Morita et al. | 548/112 |
| 5,155,100 | 10/1992 | Erion et al. | 514/119 |

FOREIGN PATENT DOCUMENTS

| | | |
|---|---|---|
| 0117429 | 9/1984 | European Pat. Off. |
| 0054862 | 11/1985 | European Pat. Off. |
| 0320118 | 6/1989 | European Pat. Off. |
| 0401963 | 12/1990 | European Pat. Off. |
| 0419327 | 3/1991 | European Pat. Off. |
| 0141930 | 5/1980 | German Democratic Rep. |
| 2207351 | 2/1988 | United Kingdom |

OTHER PUBLICATIONS

Research Communications in Chemical Pathology & Pharmacology, vol. 52, No. 1, 81 (1986).
Medicinal Research Reviews, vol. 5, No. 4, 483-531 (1985).

Primary Examiner—Mary C. Lee
Assistant Examiner—Michael G. Ambrose
Attorney, Agent, or Firm—Norbert Gruenfeld

[57] ABSTRACT

The present invention relates to the N-phosphonomethyl-biaryl substituted amino acid derivatives of formula I

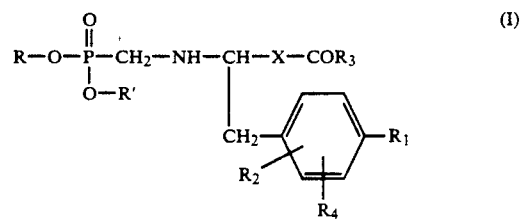

wherein X represents a direct bond, $C_{1-4}$-alkylene or $C_2$-$C_4$-alkenylene; R and R' represent independently hydrogen, carbocyclic aryl, 6-tetrahydronaphthyl, 5-indanyl, α-(trichloromethyl, carboxyl, esterified carboxyl or amidated carboxyl)substituted-(lower alkyl or aryl-lower alkyl), acyloxymethyl optionally monosubstituted on methyl carbon by $C_{1-20}$-alkyl, by $C_5$-$C_7$-cycloalkyl, by aryl or by aryl-lower alkyl; $R_1$ represents monocyclic carbocyclic or monocyclic heterocyclic aryl; $COR_3$ represents carboxyl or carboxyl derivatized in form of a pharmaceutically acceptable ester; $R_2$ and $R_4$ represent hydrogen, lower alkyl, trifluoromethyl, lower alkoxy or halogen; and pharmaceutically acceptable salts thereof; pharmaceutical compositions comprising said compounds; methods for preparation of said compounds and for the preparation of intermediates; and methods of treating disorders in mammals which are responsive to the inhibition of neutral endopeptidases by administration of said compounds to mammals in need of such treatment.

19 Claims, No Drawings

PHOSPHONO/BIARYL SUBSTITUTED AMINO ACID DERIVATIVES

SUMMARY OF THE INVENTION

Endogenous atrial natriuretic peptides (ANP), also called atrial natriuretic factors (ANF) have diuretic, natriuretic and vasorelaxant functions in mammals. The natural ANF peptides are metabolically inactivated, in particular by a degrading enzyme which has been recognized to correspond to the enzyme neutral endopeptidase (NEP, EC 3.4. 24.11), also responsible for e.g. the metabolic inactivation of enkephalins.

The aim of the present invention is to provide novel biaryl substituted phosphonic acid derivatives described below which are useful as neutral endopeptidase (NEP) inhibitors, e.g. as inhibitors of the ANF-degrading enzyme in mammals, so as to prolong and potentiate the diuretic, natriuretic and vasodilator properties of ANF in mammals, by inhibiting the degradation thereof to less active metabolites. The compounds of the invention are thus particularly useful for the treatment of conditions and disorders responsive to the inhibition of neutral endopeptidase (EC 3.4. 24.11), particularly cardiovascular disorders, such as hypertension, renal insufficiency including edema and salt retention, pulmonary edema and congestive heart failure. By virtue of their inhibition of neutral endopeptidase, the compounds of the invention may also be useful for the treatment of pain, depression and certain psychotic conditions. Other potential indications include the treatment of angina, premenstrual syndrome, Meniere's disease, hyperaldosteronism, hypercalciuria, ascites, glaucoma, asthma and gastrointestinal disorders such as diarrhea, irritable bowel syndrome and gastric hyperacidity.

DETAILED DESCRIPTION OF THE INVENTION

The present invention relates to the N-phosphonomethyl-biaryl substituted amino acid derivatives of formula I

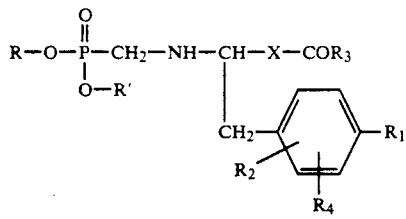

wherein X represents a direct bond, $C_{1-4}$-alkylene or $C_2$-$C_4$-alkenylene; R and R' represent independently hydrogen, carbocyclic aryl, 6-tetrahydronaphthyl, 5-indanyl, α-(trichloromethyl, carboxyl, esterified carboxyl or amidated carboxyl)substituted-(lower alkyl or aryl-lower alkyl), acyloxymethyl optionally monosubstituted on methyl carbon by $C_{1-20}$-alkyl, by $C_5$-$C_7$-cycloalkyl, by aryl or by aryl-lower alkyl; $R_1$ represents monocyclic carbocyclic or monocyclic heterocyclic aryl; $COR_3$ represents carboxyl or carboxyl derivatized in form of a pharmaceutically acceptable ester; $R_2$ and $R_4$ represent hydrogen, lower alkyl, trifluoromethyl, lower alkoxy or halogen; and pharmaceutically acceptable salts thereof; pharmaceutical compositions comprising said compounds; methods for preparation of said compounds and for the preparation of intermediates; and methods of treating disorders in mammals which are responsive to the inhibition of neutral endopeptidases by administration of said compounds to mammals in need of such treatment.

Pharmaceutically acceptable ester derivatives are preferably prodrug derivatives, such being convertible by solvolysis or under physiological conditions to the free phosphono/carboxylic acids of formula I, e.g. phosphonic acid esters as described in European Patent application No. 481,214 as prodrugs of phosphonate nucleotide analogs, and as described herein.

Compounds of formula I and derivatives thereof, depending on the nature of substituents, possess one or more asymmetric carbon atoms. The resulting diastereoisomers and optical antipodes are encompassed by the instant invention.

Particular embodiments of the invention relate to the compounds of the invention wherein X represents a direct bond, alkylene grouping and an alkenylene grouping, respectively, as defined herein.

Preferred are the compounds of formula I wherein X represents a direct bond, $C_{1-4}$-alkylene or $C_2$-$C_{14}$-alkenylene; R and R' independently represent hydrogen, carbocyclic aryl, α-(trichloromethyl, carboxyl, esterified carboxyl or amidated carboxyl) substituted-(lower alkyl or aryl-lower alkyl), (carbocyclic aroyloxy or $C_1$-$C_{20}$-alkanoyloxy)methyl optionally substituted on the methyl carbon by lower alkyl, by $C_5$, $C_6$ or $C_7$-cycloalkyl or by carbocyclic aryl; $R_1$ represents phenyl or phenyl mono- or disubstituted by lower alkyl, lower alkoxy, halogen or trifluoromethyl; or $R_1$ represents pyridyl, thienyl or furanyl, each optionally substituted by lower alkyl; $R_2$ represents hydrogen; $COR_3$ represents carboxyl or carboxyl derivatized in form of a pharmaceutically acceptable ester; $R_4$ represents hydrogen, lower alkyl, lower alkoxy, halogen or trifluoromethyl; and pharmaceutically acceptable salts thereof.

Particularly preferred are above said compounds of formula I wherein R and R' independently represent hydrogen, lower-alkanoyloxymethyl or lower-alkanoyloxymethyl substituted on methyl by lower alkyl, by cyclohexyl, by cyclopentyl or by phenyl.

Also particularly preferred are said compounds of formula I wherein R and R' independently represent hydrogen, 5-indanyl, phenyl, or phenyl substituted by one, two or three substituents selected from lower alkyl, halogen, lower alkoxy, lower alkanoylamino, trifluoromethyl, lower alkyl-(thio, sufinyl or sulfonyl) and lower alkoxycarbonyl.

Also particularly preferred are said compounds of formula I wherein R and R' independently represent hydrogen or α-(carboxy, lower alkoxycarbonyl, carbocyclic arylmethoxycarbonyl, aminocarbonyl, mono- or di-lower alkylaminocarbonyl or trichloromethyl) substituted-(lower alkyl or carbocyclic aryl-lower alkyl); and pharmaceutically acceptable salts thereof.

Advantageously, R and R' are either identical, or one of R and R' represents hydrogen while the other of R and R' has any of the other meanings as defined herein.

Also particularly preferred are the said compounds of formula I wherein $COR_3$ represents carboxyl, lower alkoxycarbonyl, (carbocyclic or heterocyclic aryl)-lower alkoxycarbonyl, (di-lower alkylamino, N-lower alkylpiperazino, morpholino, pyrrolidino, piperidino or perhydrazepino)-$C_2$ to $C_4$-alkoxycarbonyl, dihydroxypropyloxycarbonyl protected in form of a ketal, 5-indanyloxycarbonyl, α-(lower alkoxycarbonyl or di-lower alkylaminocarbonyl)-lower alkoxycarbonyl or 1-(lower alkanoyloxy)-lower alkoxycarbonyl; and pharmaceutically acceptable salts thereof.

Further preferred are any said compounds of formula I having a free carboxyl group, i.e. wherein $COR_3$ represents carboxyl; and pharmaceutically acceptable salts thereof.

A particular embodiment of the invention relates to the compounds of formula II

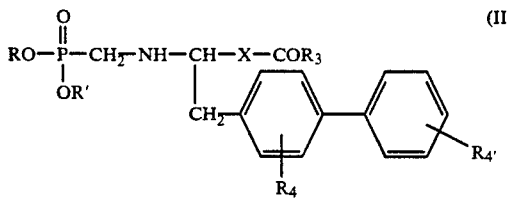

wherein X represents a direct bond, $C_{1-2}$-alkylene or $C_2$-alkenylene; R and R' independently represent hydrogen, carbocyclic aryl, 5-indanyl, α-(carboxyl, lower alkoxycarbonyl, carbocyclic arylmethoxycarbonyl, aminocarbonyl or mono- or di-lower alkylaminocarbonyl or trichloromethyl) substituted-(lower alkyl or carbocyclic aryl-lower alkyl), or

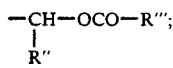

R'' represents hydrogen, $C_1$-$C_{20}$-alkyl, $C_5$, $C_6$ or $C_7$-cycloalkyl or carbocyclic aryl; R''' represents $C_1$-$C_{20}$-alkyl, $C_5$, $C_6$ or $C_7$-cycloalkyl, carbocyclic aryl or carbocyclic aryl-lower alkyl; $COR_3$ represents carboxyl, $C_1$-$C_{20}$-alkoxycarbonyl, (carbocyclic or heterocyclic aryl)-lower alkoxycarbonyl, (di-lower alkylamino, N-lower alkylpiperazino, morpholino, pyrrolidino, piperidino or perhydrazepino)-$C_2$ to $C_4$-alkoxycarbonyl, dihydroxypropyloxycarbonyl protected in form of a ketal, 5-indanyloxycarbonyl, α-(lower alkoxycarbonyl or di-lower alkylaminocarbonyl)-lower alkoxycarbonyl; $R_4$ and $R_4'$ represent hydrogen, lower alkyl, lower alkoxy, halogen or trifluoromethyl; and pharmaceutically acceptable salts thereof.

Preferred are said compounds of formula II wherein $COR_3$ represents carboxyl; also preferred are said compounds wherein $R_4$ and $R_4'$ represent hydrogen or lower alkoxy; and other symbols have meaning as defined above; and pharmaceutically acceptable salts thereof.

Advantageously, R and R' are either identical, or one of R and R' represents hydrogen while the other of R and R' has any of the other meanings as defined herein.

A preferred embodiment of the invention relates to a compound of formula III

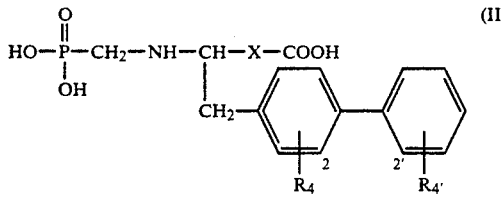

wherein X represents a direct bond, methylene or ethenylene; $R_4$ and $R_4'$ represent hydrogen or $C_1$-$C_3$alkoxy; and pharmaceutically acceptable mono-, di- or tri-ester derivatives thereof in which one, two or three of the acidic hydroxy groups of the carboxyl and phosphono functional groups are esterified in form of a mono-, di- or tri-pharmaceutically acceptable ester; pharmaceutically acceptable salts thereof; and optical or stereoisomers thereof.

The pharmaceutically acceptable ester derivatives are preferably prodrug ester derivatives, such being convertible by solvolysis or under physiological conditions to the free acid of formula III.

Preferred embodiments are compounds of formula IIIa and IIIb

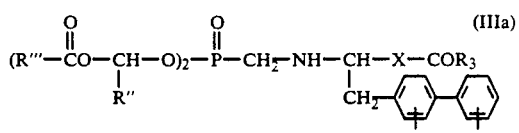

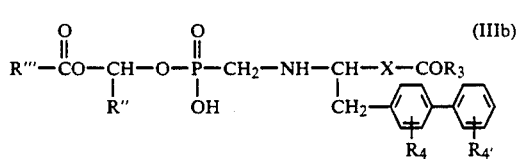

wherein X represents a direct bond, methylene or ethenylene; R'' and R''' independently represent hydrogen, $C_1$-$C_{20}$-straight chain or branched alkyl, cyclohexyl, cyclopentyl or phenyl; $COR_3$ represents carboxyl; or $COR_3$ represents carboxyl esterified in form of a pharmaceutically acceptable prodrug ester preferably selected from $C_1$-$C_{20}$-alkoxycarbonyl, (carbocyclic or heterocyclic aryl)-methoxycarbonyl, (di-lower alkylamino)-$C_2$ to $C_4$-alkoxycarbonyl, dihydroxypropyloxycarbonyl protected in form of a ketal, (lower alkoxycarbonyl or di-lower alkylaminocarbonyl)-methoxycarbonyl, 5-indanyloxycarbonyl and 1-(lower alkanoyloxy)-lower alkoxycarbonyl; $R_4$ and $R_4'$ represent hydrogen or $C_1$-$C_3$alkoxy; and pharmaceutically acceptable salts thereof.

Preferred in turn are said compounds of formula IIIa wherein R'' and R''' have meaning as defined above and $COR_3$ represents carboxyl. Also preferred are said compounds of formula IIIb wherein R'' and R''' have meaning as defined above and $COR_3$ represents carboxyl.

Other preferred embodiments are the compounds of formula IIIc, IIId, IIIe and IIIf

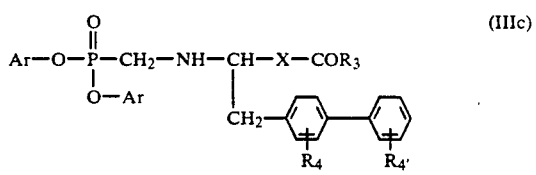

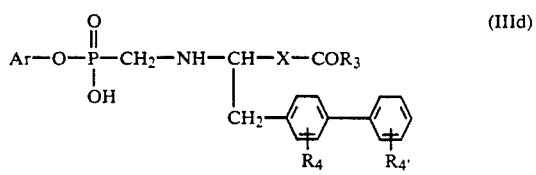

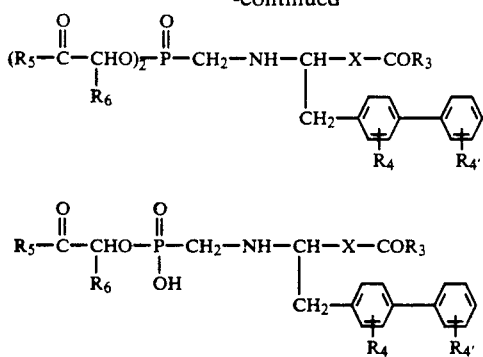

wherein X represents a direct bond, methylene or ethenylene; Ar represents phenyl or phenyl substituted by lower alkyl, lower alkoxy, halogen, trifluoromethyl, lower alkanoylamino, lower alkyl-(thio, sulfinyl or sulfonyl) or lower alkoxycarbonyl; or Ar represents 5-indanyl; $R_5$ represents hydroxy, lower alkoxy, aryl-lower alkoxy or di-lower alkylamino; $R_6$ represents hydrogen or lower alkyl; $COR_3$ represents carboxyl; or $COR_3$ represents carboxyl esterified in form of a pharmaceutically acceptable prodrug ester preferably selected from $C_1$-$C_{20}$-alkoxycarbonyl, (carbocyclic or heterocyclic aryl)-methoxycarbonyl, (di-lower alkylamino)-$C_2$ to $C_4$-alkoxycarbonyl, dihydroxypropyloxycarbonyl protected in form of a ketal, (lower alkoxycarbonyl or di-lower alkylaminocarbonyl)-methoxycarbonyl, 5-indanyloxycarbonyl, 1-(lower alkanoyloxy)-lower alkoxycarbonyl; $R_4$ and $R_4'$ represent hydrogen or $C_1$-$C_3$alkoxy; and pharmaceutically acceptable salts thereof.

Preferred in turn are said compounds of formula IIIc, IIId, IIIe and IIIf wherein $COR_3$ represents carboxyl; and pharmaceutically acceptable salts thereof.

Also preferred are any of the above compounds wherein X is a direct bond.

A further particular embodiment of the invention relates to compounds having the configuration at the asymmetric center corresponding to (S)-biarylalanine.

Compounds of the invention, depending on the nature of substituents, can exist in the form of geometric isomers, racemates, diastereoisomers, pure enantiomers or mixtures thereof, all of which are within the scope of the invention.

The definitions used herein, unless denoted otherwise, have the following meanings within the scope of the present invention.

Carbocyclic aryl represents preferably monocyclic carbocyclic aryl or optionally substituted naphthyl.

Monocyclic carbocyclic aryl represents optionally substituted phenyl, being preferably phenyl or phenyl substituted by one to three substituents, such being advantageously lower alkyl, hydroxy, lower alkoxy, lower alkanoyloxy, halogen, cyano, trifluoromethyl, lower alkanoylamino, lower alkyl-(thio, sulfinyl or sulfonyl) or lower alkoxycarbonyl.

Optionally substituted naphthyl represents 1- or 2-naphthyl or 1- or 2-naphthyl preferably substituted by lower alkyl, lower alkoxy or halogen.

Heterocyclic aryl represents preferably monocyclic heterocyclic aryl such as optionally substituted thienyl, furanyl, pyridyl, pyrrolyl or N-lower alkylpyrrolyl.

Optionally substituted furanyl represents 2- or 3-furanyl or 2- or 3-furanyl preferably substituted by lower alkyl.

Optionally substituted pyridyl represents 2-, 3- or 4-pyridyl or 2-, 3- or 4-pyridyl preferably substituted by lower alkyl, halogen or cyano.

Optionally substituted thienyl represents 2- or 3-thienyl or 2- or 3-thienyl preferably substituted by lower alkyl.

Aryl as in aryl-lower alkyl is preferably phenyl or phenyl substituted by one or two of lower alkyl, lower alkoxy, hydroxy, lower alkanoyloxy, halogen, trifluoromethyl, cyano, lower alkanoylamino or lower alkoxycarbonyl.

Aryl-lower alkyl is advantageously benzyl or phenethyl optionally substituted by one or two of lower alkyl, lower alkoxy, hydroxy, lower alkanoyloxy, halogen or trifluoromethyl.

The term "lower" referred to herein in connection with organic radicals or compounds respectively defines such with up to and including 7, preferably up and including 4 and advantageously one or two carbon atoms. Such may be straight chain or branched.

A lower alkyl group preferably contains 1-4 carbon atoms and represents for example ethyl, propyl, butyl or advantageously methyl.

A lower alkoxy group preferably contains 1-4 carbon atoms and represents for example methoxy, propoxy, isopropoxy or advantageously ethoxy.

The term $C_5$-$C_7$-cycloalkyl represents a saturated cyclic hydrocarbon radical which preferably contains 5 to 7 ring carbons and is, preferably cyclopentyl or cyclohexyl.

The term cycloalkyl(lower)alkyl represents preferably 1- or 2-(cyclopentyl or cyclohexyl)ethyl, 1-, 2- or 3-(cyclopentyl or cyclohexyl)propyl, or 1-, 2-, 3- or 4-(cyclopentyl or cyclohexyl)-butyl.

Amino-lower alkyl represents preferably amino-(ethyl, propyl or butyl), particularly omega-amino-(ethyl, propyl or butyl).

A di-lower alkylamino group preferably contains 1-4 carbon atoms in each lower alkyl portion and represents, for example, N,N-dimethylamino, N-methyl-N-ethylamino and advantageously N,N-diethylamino.

A lower alkoxycarbonyl group preferably contains 1 to 4 carbon atoms in the alkoxy portion and represents, for example, methoxycarbonyl, propoxycarbonyl, isopropoxycarbonyl or advantageously ethoxycarbonyl.

Lower alkoxycarbonyl-lower alkoxy represents advantageously e.g. 1-(ethoxycarbonyl)ethoxy or ethoxycarbonylmethoxy.

Di(lower)alkylamino-lower alkoxy advantageously represents diethylaminoethoxy.

Halogen (halo) preferably represents fluoro or chloro, but may also be bromo or iodo.

Lower alkanoyl is preferably acetyl, propionyl, butyryl, or pivaloyl.

Lower alkanoyloxy is preferably acetoxy, pivaloyloxy or propionyloxy.

Acylamino represents preferably lower alkanoylamino, aroylamino, or aryl-lower alkoxycarbonylamino such as benzyloxycarbonylamino.

Lower alkanoylamino is preferably acetamido or propionamido.

Aroyl is preferably benzoyl or benzoyl substituted on the benzene ring by lower alkyl, lower alkoxy, halogen or trifluoromethyl.

Acyl represents preferably lower alkanoyl, carbocyclic aryl-lower alkanoyl, aroyl, lower alkoxycarbonyl or aryl-lower alkoxycarbonyl, advantageously lower alkanoyl. Lower alkoxycarbonyl for acyl is preferably t-butoxycarbonyl (abbreviated t-BOC). Aryl-lower alkoxycarbonyl for acyl is preferably benzyloxycarbonyl (abbreviated CBZ).

Lower alkylidene is preferably isopropylidene.

Cycloalkylidene is preferably cyclohexylidene.

Carboxyl esterified in form of a pharmaceutically acceptable ester represents advantageously a prodrug ester that may be convertible by solvolysis or under physiological conditions to the free carboxylic acid, such being preferably lower alkoxycarbonyl, advantageously lower alkoxycarbonyl; (amino, acylamino, mono- or di-lower alkylamino)-lower alkoxycarbonyl; carboxy- lower alkoxycarbonyl, e.g. alpha-carboxy-lower alkoxycarbonyl; lower alkoxycarbonyl-lower alkoxycarbonyl, e.g. alpha-lower alkoxycarbonyl-lower alkoxycarbonyl; α-(di-lower alkylamino, amino, mono-lower alkylamino, morpholino, piperidino, pyrrolidino, 1-lower alkylpiperazino)-carbonyl-lower alkoxycarbonyl; aryl-lower alkoxycarbonyl, preferably optionally (halo, lower alkyl or lower alkoxy)-substituted benzyloxycarbonyl, or pyridyl-methoxycarbonyl; 1-(hydroxy, lower alkanoyloxy or lower alkoxy)-lower alkoxycarbonyl, e.g. pivaloyloxymethoxycarbonyl; (hydroxy, lower alkanoyloxy or lower alkoxy)-lower alkoxymethoxycarbonyl; bicycloalkoxycarbonyl-lower alkoxycarbonyl, e.g. bicyclo-[2,2,1]-heptyloxycarbonyl-lower alkoxycarbonyl, especially bicyclo-[2,2,1]-heptyloxycarbonylmethoxycarbonyl such as bornyloxycarbonylmethoxycarbonyl; 1-(lower alkoxycarbonyloxy)-lower alkoxycarbonyl; 5-indanyloxycarbonyl; 3-phthalidoxycarbonyl and (lower alkyl, lower alkoxy or halo)-substituted 3-phthalidoxycarbonyl; dihydroxypropyloxycarbonyl wherein hydroxy groups are free or are protected in the form of ketals, e.g. a lower alkylidene, a benzylidene or a 5- or 6-membered cycloalkylidene derivative, advantageously being (2,2-dimethyl-1,3-dioxolan-4-yl)-methoxycarbonyl.

Carboxyl esterified in form of a pharmaceutically acceptable prodrug ester represents most advantageously $C_1$-$C_4$-alkoxycarbonyl, benzyloxycarbonyl optionally substituted on phenyl by lower alkyl, lower alkoxy, halo or trifluoromethyl, 1-($C_2$-$C_4$-alkanoyloxy)-ethoxycarbonyl, (2,2-dimethyl-1,3-dioxolan-4-yl)-methoxycarbonyl, 5-indanyloxycarbonyl, 1-($C_1$-$C_4$-alkoxycarbonyloxy)-ethoxycarbonyl or 3-pyridylmethoxycarbonyl.

Esterified carboxyl as such represents advantageously lower alkoxycarbonyl or aryl-lower alkoxycarbonyl.

Amidated carboxyl represents advantageously aminocarbonyl, mono- or di-lower alkylaminocarbonyl.

Phosphono derivatized in the form of a pharmaceutically acceptable ester represents mono- or di-esters thereof, preferably phosphono derivatized as mono- or di-prodrug esters such as mono- or di-carbocyclic arylphosphono, e.g. mono- or di-phenylphosphono; mono- or di-5-indanylphosphono; mono- or di-acyloxymethylphosphono optionally substituted on methyl by $C_1$-$C_{20}$-alkyl, by $C_5$-$C_7$-cycloalkyl, by aryl (e.g. phenyl) or by aryl-lower alkyl (e.g. benzyl), and wherein acyloxy represents $C_1$-$C_{20}$-alkanoyloxy, $C_5$-$C_7$-cycloalkanoyloxy, carbocyclic aroyloxy or carbocyclic aryl-lower alkanoyloxy; as mono- or di-(α-lower alkoxycarbonyl-lower alkyl)phosphono; as mono- or di-(α-di-lower alkylaminocarbonyl-lower alkyl)phosphono; also as mono- or di-(α-trichloromethyl-lower alkyl)phosphono.

Phosphono derivatized as a mono- or di-prodrug ester relates to a pharmaceutically acceptable mono- or di-phosphono ester that may be convertible by solvolysis or under physiological conditions to phosphono (the free phosphonic acid), such as illustrated above.

Pharmaceutically acceptable salts are pharmaceutically acceptable acid addition salts for any basic compounds of the invention or salts derived from pharmaceutically acceptable bases for any acidic compounds of the invention.

Pharmaceutically acceptable salts of basic compounds of the invention are acid addition salts, which are preferably such of therapeutically acceptable inorganic or organic acids, such as strong mineral acids, for example hydrohalic, e.g. hydrochloric or hydro-bromic acid, sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, 1,2-ethanedisulfonic acid, benzenesulfonic, p-toluenesulfonic, naphthalenesulfonic, sulfanilic, cyclohexylsulfamic acid, or ascorbic acid.

Pharmaceutically acceptable salts of the acidic compounds of the invention, e.g. those having a free carboxyl group or a free phosphono hydroxyl group are salts formed with pharmaceutically acceptable bases, e.g. alkali metal salts (e.g. sodium, potassium salts), alkaline earth metal salts (e.g. magnesium, calcium salts), amine salts (e.g. ethanolamine, diethanolamine, triethanolamine, tromethamine salts).

The novel compounds of the invention are pharmacologically potent neutral endopeptidase enzyme inhibitors which inhibit e.g. the degradation of atrial natriuretic factors (ANF) in mammals. They thus potentiate the diuretic and natriuretic effect of exogenous or endogenous ANF in mammals.

The compounds of the invention are thus particularly useful in mammals as diuretic, natriuretic (saluretic) and antihypertensive agents for the treatment of e.g. hypertension, congestive heart failure and edema.

As neutral endopeptidase inhibitors, the compounds of the invention also inhibit enkephalinase so as to inhibit the degradation of endogenous enkephalins and may thus also be useful for the treatment of pain in mammals.

The above-cited properties are demonstrable in vitro and in vivo tests, using advantageously mammals, e.g. mice, rats, dogs, monkeys or isolated organs, tissues and preparations thereof. Said compounds can be applied in vitro in the form of solutions, e.g. preferably aqueous solutions, and in vivo either enterally, parenterally, advantageously intravenously, e.g. as a suspension or in aqueous solution. The dosage in vitro may range between about $10^{-5}$ molar and $10^{-9}$ molar concentrations. The dosage in vivo may range depending on the route of administration, between about 0.01 and 50 mg/kg, advantageously between about 1.0 and 25 mg/kg.

The analgesic activity can be determined by measuring the potentiation of the analgesic effects of enkephalin and derivatives thereof, and by classical analgesic tests, such as the phenyl-p-benzoquinone induced writing test [J. Pharmacol. Exp. Therap. 125, 237 (1959)] and the hot plate test in the mouse [J. Pharmacol. Exp. Therap. 107, 385 (1953).

The antihypertensive activity can be determined e.g. in the DOCA-salt hypertensive rat, and/or renal hypertensive rat or dog model.

The diuretic (saluretic) activity can be determined in standard diuretic screens, e.g. as described in "New Antihypertensive Drugs", Spectrum Publications, 1976, pages 307-321, or by measuring the potentiation of atrial natriuretic factor-induced natriuresis and diuresis in the rat.

The potentiation of ANF can also be determined by measuring the increase in ANF plasma level achieved.

The in vitro inhibition of neutral endopeptidase (NEP, EC 3.4.24.11) can be determined as follows:

The test compound is dissolved in dimethyl sulfoxide or 0.25M sodium bicarbonate solution, and the solution is diluted with pH 7.4 buffer to the desired concentration.

Neutral endopeptidase 3.4.24.11 activity is determined by the hydrolysis of the substrate glutaryl-Ala-Ala-Phe-2-naphthylamide (GAAP) using a modified procedure of Orlowski and Wilk (1981). The incubation mixture (total volume 125 $\mu$l) contains 4.2 $\mu$g of protein (rat kidney cortex membranes prepared by method of Maeda et al, 1983), 50 mM tris buffer, pH 7.4 at 25° C., 500 $\mu$M substrate (final concentration), and leucine aminopeptidase M (2.5 $\mu$g). The mixture is incubated for 10 minutes at 25° C. and 100 $\mu$l of fast garnet (250 $\mu$g fast garnet/ml of 10% Tween 20 in 1M sodium acetate, pH 4.2) is added. Enzyme activity is measured spectrophotometrically at 540 nm. One unit of NEP 24.11 activity is defined as 1 mmol of 2-naphthylamine released per minute at 25° C. at pH 7.4. IC$_{50}$ values are determined, i.e. the concentration of test compound required for 50% inhibition of the release of 2-naphthylamine.

Neutral endopeptidase activity can also be determined using ANF as a substrate. Atrial natriuretic factor degrading activity is determined by measuring the disappearance of rat-ANF (r-ANF) using a 3 minute reverse phase-HPLC separation. An aliquot of the enzyme in 50 mM Tris HCl buffer, pH 7.4, is preincubated at 37° C. for 2 minutes and the reaction is initiated by the addition of 4 nmol of r-ANF in a total volume of 50 $\mu$l. The reaction is terminated after 4 minutes with the addition of 30 $\mu$l of 0.27% trifluoroacetic acid (TFA). One unit of activity is defined as the hydrolysis of 1 nmol of r-ANF per minute at 37° C. at pH 7.4. IC$_{50}$ values are determined, i.e. the concentration of test compound required for 50% inhibition of the hydrolysis of ANF.

In vitro testing is most appropriate for the free phosphono/carboxylic acids of the invention.

Illustrative of the invention, (S)-2-(phosphonomethylamino)-3-(4-biphenylyl)-propionic acid demonstrates an IC$_{50}$ of about 15 nM in the GAAP in vitro assay.

The effect of the compounds of the invention on rat plasma ANF concentration can be determined as follows:

Male Sprague-Dawley rats (275-390 g) are anesthetized with ketamine (150 mg/kg)/acepromazine (10%) and instrumented with catheters in the femoral artery and vein to obtain blood samples and infuse ANF, respectively. The rats are tethered with a swivel system and are allowed to recover for 24 hours before studied in the conscious, unrestrained state.

In this assay, plasma ANF levels are determined in the presence and absence of NEP inhibition. On the day of study, all rats are infused continuously with ANF at 450 ng/kg/min. i.v. for the entire 5 hours of the experiment. Sixty minutes after beginning the infusion, blood samples for baseline ANF measurements are obtained (time 0) and the rats are then randomly divided into groups treated with the test compound or vehicle. Additional blood samples are taken 30, 60, 120, 180 and 240 minutes after administration of the test compound.

Plasma concentrations are determined by a specific radioimmunoassay. The plasma is diluted ($\times$12.5, $\times$25 and $\times$50) in buffer containing: 50 mM Tris (pH 6.8), 154 mM NaCl, 0.3% bovine serum albumin, 0.01% EDTA. One hundred microliters of standards [rANF (99-126)] or samples are added to 100 $\mu$l of rabbit anti-rANF serum and incubated at 4° C. for 16 hours. Ten thousand cpm of [$^{125}$I]rANF are then added to the reaction mixture which is incubated at 4° C. for an additional 24 hours. Goat anti-rabbit IgG serum coupled to paramagnetic particles is added to the reaction mixture and bound [$^{125}$I]rANF is pelleted by exposing the mixture to an attracting magnetic rack. The supernatant is decanted and the pellets counted in a gamma counter. All determinations are performed in duplicate. Plasma ANF levels are expressed as a percent of those measured in vehicle-treated animals which received ANF alone (450 ng/kg/min i.v.).

The antihypertensive effect can be determined in desoxycorticosterone acetate (DOCA)-salt hypertensive rats.

DOCA-salt hypertensive rats (280-380 g) are prepared by the standard method. Rats underwent a unilateral nephrectomy and one week later are implanted with silastic pellets containing 100 mg/kg of DOCA. The rats are maintained on 1% NaCl/0.2% KCl drinking water for three to five weeks until sustained hypertension is established. The antihypertensive activity is evaluated at this time.

Two days before an experiment, the rats are anesthetized with methoxyflurane and instrumented with catheters in the femoral artery to measure arterial blood pressure. Forty-eight hours later, baseline arterial pressure and heart rate are recorded during a 1 hour period. The test compound or vehicle is then administered and the same cardiovascular parameters are monitored for an additional 5 hours.

The potentiation of the natriuretic effect of ANF can be determined as follows:

Male Sprague-Dawley rats (280-360 g) are anesthetized with Inactin (100 mg/kg i.p.) and instrumented with catheters in the femoral artery, femoral vein and urinary bladder to measure arterial pressure, administer ANF and collect urine, respectively. A continuous infusion of normal saline (33 $\mu$l/min) is maintained throughout the experiment to promote diuresis and sodium excretion. The experimental protocol consists of an initial 15 minute collection period (designated as pre-control) followed by three additional collection periods. Immediately after completion of the pre-control period, test compound or vehicle is administered; nothing is done for the next 45 minutes. Then, blood pressure and renal measurements are obtained during a second collection period (designated control; 15 min). At the conclusion of this period, ANF is administered (1 $\mu$g/kg i.v. bolus) to all animals and arterial pressure and renal parameters are determined during two consecutive 15 minutes collection periods.

Mean arterial pressure, urine flow and urinary sodium excretion are determined for all collection periods. Blood pressure is measured with a Gould p50 pressure transducer, urine flow is determined gravimetrically, sodium concentration is measured by flame photometry, and urinary sodium excretion is calculated as the product of urine flow and urine sodium concentration.

The compounds of the invention are thus particularly useful as inhibitors of neutral endopeptidase, enhancing the potency and duration of action of atrial natriuretic peptide(s). The compounds are therefore particularly useful for the treatment of cardiovascular disorders such as hypertension, edema and salt retention, and cardiac conditions such as congestive heart failure.

The compounds of the invention can be prepared using processes described and illustrated below:

(a) condensing under reductive amination conditions a compound of the formula IV

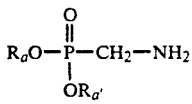
(IV)

wherein $R_2$ has meaning as defined herein, and Ra and Ra' have meaning as defined for R and R' in formula I, and $R_a$ and $R_a'$ may in addition represent lower alkyl or aryl-lower alkyl, with a compound of formula V

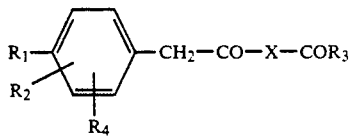
(V)

wherein $R_1$, $R_2$, $R_4$, X and $COR_3$ have meaning as defined hereinabove;

(b) reacting a compound of formula VI

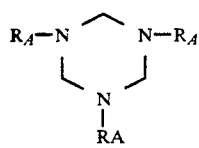
(VI)

wherein $R_A$ represents the grouping

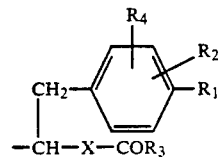
($R_A$)

wherein $R_1$, $R_2$, and $R_4$ have meaning as defined above, and $COR_3$ represents esterified carboxyl; with a diester of phosphonic (phosphorous) acid, also named as a disubstituted phosphite, of formula VII

(VII)

wherein $R_b$ and $R_b'$ have meaning as defined herein for R and R', except that $R_b$ and $R_b'$ do not represent hydrogen, and $R_b$ and $R_b'$ may in addition represent lower alkyl or aryl-lower alkyl; or reacting a said intermediate of formula VI with tris(trimethylsilyl)phosphite, P[O-Si(CH$_3$)$_3$]$_3$, in the presence of e.g. zinc chloride or TiCl$_4$ followed by an alcohol, e.g. methanol, to obtain a compound of formula I wherein R and R' represent hydrogen; or (c) reacting a compound of formula VIII

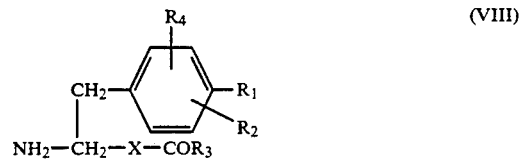
(VIII)

wherein $COR_3$ represents esterified carboxyl and $R_1$, $R_2$, X and $R_4$ have meaning as defined above, with a reactive esterified derivative of a hydroxymethylphosphonic acid derivative of the formula IX

(IX)

wherein $R_c$ and $R_c'$ represent lower alkyl or aryl-lower alkyl, e.g. optionally substituted benzyl, and Z represents a leaving group, e.g. a reactive esterified hydroxyl group, such as trifluoromethylsulfonyloxy; and (d) converting any compound obtained in any said process, in which any of $R_a$, $R_b$, $R_c$, $R_a'$, $R_b'$ and $R_c'$ represent lower alkyl or aryl-lower alkyl, to a corresponding product of the invention in which such have meaning as defined for R and R' in formula I; and in above said processes, if temporarily protecting any interfering reactive group(s), removing said protecting group(s), and then isolating the resulting compound of the invention; and, if desired, converting any resulting compound of the invention into another compound of the invention; and/or, if desired, converting a free carboxylic or phosphonic acid function into a pharmaceutically acceptable ester derivative, or converting a resulting ester into the free acid or into another ester derivative; and/or, if desired, converting a resulting free compound into a salt or a resulting salt into the free compound or into another salt, and/or, if desired, separating a mixture of isomers or racemates obtained into the single isomers or racemates, and/or, if desired, resolving a racemate into the optical antipodes.

In starting compounds and intermediates which are converted to the compounds of the invention in a manner described herein, functional groups present, such as phosphonyl, carboxyl, amino and hydroxy groups, are optionally protected by conventional protecting groups that are common in preparative organic chemistry. Protected phosphonyl, carboxyl, amino and hydroxy groups are those that can be converted under mild conditions into free phosphonyl, carboxyl, amino and hydroxy groups without other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (phosphonyl, carboxyl group, amino group etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, New York 1973, T. W. Greene et al, "Protective Groups in Organic Synthesis", Wiley, New York 1991, and also in "The Peptides", Vol. I, Schroeder and Luebke, Academic Press, London, New York, 1965.

The preparation of compounds of the invention according to process (a) under conditions of reductive amination, involves the reductive amination of the appropriate keto acid or derivative thereof of formula V with a diester of aminomethylphosphonic acid of formula IV (e.g. the dimethyl ester), in the presence of a reducing agent such as hydrogen or sodium cyanoborohydride under standard reductive amination conditions, e.g. as illustrated in the examples to obtain compounds of formula Ia

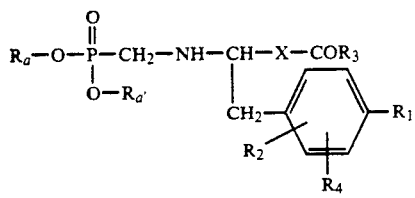

wherein $R_1$, $R_2$, $R_4$, $R_a$, $R_a'$ and $COR_3$ have meaning as defined above.

The aminomethylphosphonic acid diesters of formula IV are prepared according to methods known in the art, for instance by reaction of phthalimidomethyl bromide with trimethylphosphite [P(OCH$_3$)$_3$] to obtain the corresponding dimethyl phthalimidomethyl phosphonate which is converted with hydrazine to dimethyl aminomethylphosphonate.

As to the keto acids of formula V, such are known in the art or are e.g. in turn prepared by methods analogous to those used for the preparation of substituted pyruvic acids, when X is a direct bond, by condensation of e.g. the methyl ester of a biarylacetic acid with diethyl oxalate in the presence of a base, e.g. potassium t-butoxide, followed by hydrolytic decarboxylation.

The preparation of compounds of the invention according to process (b), i.e. the condensation of a hexahydrotriazine derivative of formula VI with a phosphonic acid diester of formula VII (the type of reaction is illustrated in U.S. Pat. No. 4,053,505 for the preparation of N-phosphonomethylglycine) is carried out in an inert solvent such as toluene or benzene, preferably at elevated temperature, to yield e.g. a compound of formula Ib

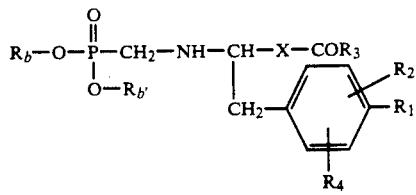

wherein $R_1$, $R_2$, $R_4$, X, $COR_3$, $R_b$ and $R_b'$ have meaning as defined above.

Condensation of a compound of formula VI with tris(trimethylsilyl)phosphite can be carried out as known in the art for the type of reaction involved, e.g. as illustrated in Bull. Korean Chem. Soc. 1990, 11, 485 and Polish J. Chem. 1981, 55, 643.

The phosphonic acid (phosphite) diesters of formula VII are known or can be prepared according to methods in the literature, e.g. U.S. Pat. No. 3,329,742 for the preparation of diaryl phosphites.

Tris(trimethylsilyl)phosphite is commercially available or can be prepared as described in J. Am. Chem. Soc. 1974, 96, 7363.

Unsymmetrical phosphonic acid diesters can be prepared by first treating a symmetrical diester, e.g. dibenzyl phosphite, with aqueous base, e.g. aqueous tetramethyl ammonium hydroxide, to obtain a monoester, e.g. monobenzyl phosphite. This can be treated e.g. with an appropriate alkyl halide corresponding to R or R' in formula I, for example an α-acyloxyalkyl bromide, to obtain a compound of formula VII wherein $R_b$ is benzyl and $R_b'$ is α-acyloxyalkyl. Alternatively, monobenzyl phosphite can first be converted to e.g. a mixed anhydride (e.g. with pivaloyl chloride) which is then reacted with an appropriate alcohol or phenol corresponding to R or R' in formula I to obtain a corresponding unsymmetrical diester of formula VII. The resulting condensation product of formula Ib wherein either $R_b$ or $R_b'$ represents benzyl can then be converted to a compound of formula I wherein either R or R' represents hydrogen by selective catalytic hydrogenolysis of the benzyl substituent.

The hexahydrotriazines of formula VI, e.g. when X is a direct bond, can be prepared as follows:

An N-acylbiarylalanine ester, e.g. N-t-butoxycarbonyl-4-biphenylalanine methyl ester, prepared as described herein, is selectively hydrolyzed with dilute base to the corresponding N-acylbiarylalanine, e.g. N-t-butoxycarbonyl-4-biphenylalanine. The carboxylic acid is converted to an ester of formula VIII

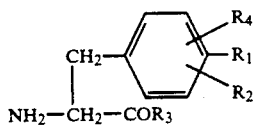

wherein $COR_3$ represents esterified carboxyl, and $R_1$, $R_2$ and $R_4$ have meaning as defined above.

Condensation of an ester of formula VIII, according to the general known process for the synthesis of hexahydrotriazine derivatives, e.g. as described in J. Org. Chem. 53, 3113 (1988), e.g. with formaldehyde, preferably 37% aqueous formaldehyde, advantageously in a solvent such as a mixture of ethyl acetate and water at room temperature, yields a corresponding hexahydrotriazine derivative of formula VI.

The preparation of the compounds of the invention according to process (c) involves the condensation of a compound of formula VIII, e.g. a lower alkyl or aryl-lower alkyl ester of the appropriate biarylalanine with a reactive esterified derivative of hydroxymethylphosphonic acid of formula IX, e.g. dimethyl (trifluoromethylsulfonyloxy)-methylphosphonate (prepared e.g. according to Organic Synthesis 64, 80 (1985) and Tetrahedron Letters 1986, 1477) in a polar solvent, such as methylene chloride, in the presence of a base, e.g. a tertiary amine such as diisopropylethylamine, at a temperature near room temperature. The resulting carboxylic acid ester can be selectively hydrolyzed to the carboxylic acid according to methods for carboxylic acid ester hydrolysis well known in the art.

The biarylalanine starting materials (when X is a direct bond) are either known in the art or can be prepared according to methods reported in the art.

Such can be transformed into the next higher homologs according to procedures known in the art or methods described herein.

For example, N-t-butoxycarbonyl-4-biphenylalanine is converted to a mixed anhydride which is treated with diazomethane followed by rearrangement of the resulting diazoketone with e.g. silver benzoate and methanol to obtain 3-(t-butoxycarbonylamino)-4-(biphenyl-4-yl)-butyric acid methyl ester.

As to the starting materials wherein X represents alkenylene, such can also be prepared from the corresponding N-protected biarylalanines. For example N-t-butoxycarbonyl-4-biphenylalanine, derivatized as a mixed anhydride, is reduced to the corresponding alcohol (e.g. with sodium borohydride) which is in turn oxidized to the aldehyde (e.g. by Swern oxidation with dimethylsufoxide and triethylamine). A Wittig type condensation with e.g. (carboethoxy-methylene)triphenylphosphorane yields the N-protected starting material of formula VIII wherein $R_1$ is phenyl, $R_2$ and $R_4$ are hydrogen and X is $-CH=CH-$.

As to the preparation of the biarylalanines as starting materials in optically active form, such can be prepared e.g. by resolution or by one of the following methods:

(a) Adapting a method described in J. Am. Chem. Soc. 113, 9276 (1991), a biarylmethanol, e.g. 4-biphenylylmethanol, is converted to a reactive derivative, e.g. the bromide, which is then condensed with an N-acyl derivative of 2,3-diphenyl-6-oxomorpholine, e.g. the N-carbobenzyloxy-(2R, 3S)-isomer, in the presence of a strong base such as sodium bis-trimethylsilylamide, to yield e.g. N-carbobenzyloxy-2(R), 3(S), 5(S)-6-oxo-2,3-diphenyl-5-(4-biphenylylmethyl)-morpholine. Catalytic hydrogenolysis, e.g. using hydrogen and palladium on charcoal as catalyst, yields the optically active (S)-(+)-4-biphenylalanine.

(b) Alternatively, using the Pd (0)-catalyzed cross-coupling reaction described by W. Shieh et al, J. Organic Chemistry, 57, 379 (1992) the substantially optically pure chiral biarylalanines, of the formula

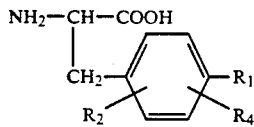

or the N-acyl and/or carboxy ester derivatives thereof wherein $R_1$, $R_2$ and $R_4$ have meaning as defined hereinabove, can be prepared by: condensing a reactive esterified optically active tyrosine derivative of the formula

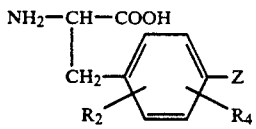

wherein the amino and carboxy groups are in protected form (as N-acyl and esterified carboxy ester derivatives), and Z represents reactive esterified hydroxy (advantageously trifluoromethylsulfonyloxy) with an aryl boronic acid in which aryl corresponds to $R_1$ as defined above, in the presence of a palladium (0) catalyst, in particular tetrakis(triphenylphosphine)palladium (0), and in the presence of an anhydrous base (such as an alkali metal carbonate), in an inert solvent (such as xylene or toluene) at an elevated temperature ranging from about 50° to 150° C., and removing any protecting groups as required.

For example, N-t-butoxycarbonyl-tyrosine methyl ester is first converted to N-t-butoxycarbonyl-4-trifluoromethylsulfonyloxy-phenylalanine methyl ester (N-t-butoxycarbonyltyrosine triflate methyl ester). This compound is then condensed with an arylboronic acid (e.g. phenylboronic acid) in the presence of anhydrous potassium carbonate, and tetrakis (triphenylphosphine) palladium (0) complex as catalyst, in toluene preferably at an elevated temperature, advantageously at about 100° to obtain N-t-butoxycarbonyl-4-biphenylalanine methyl ester. After N-deacylation, substantially optically pure 4-biphenylalanine methyl ester is obtained with a configuration corresponding to that of the tyrosine derivative used as starting material.

The arylboronic acids are either commercial or can be prepared as described in the literature, e.g. J. Org. Chem. 49, 5237 (1984).

The conversion according to process (d) of products obtained in the above processes, e.g. of formula Ia and Ib wherein $R_a$, $R_a'$, $R_b$ and $R_b'$, represent lower alkyl or aryl-lower alkyl to compounds of formula I can be carried out using known reagents for converting phosphonic acid esters to phosphonic acids, e.g. hydrobromic acid in glacial acetic acid, trimethylsilyl bromide, or by catalytic hydrogenation when such represent optionally substituted benzyl.

The compounds of the invention so obtained, can be converted into each other according to conventional methods. Thus, for example, resulting carboxylic acid esters may be hydrolyzed with aqueous alkalies, such as alkali metal carbonates or hydroxides. Resulting free acids may be esterified with e.g. unsubstituted or substituted alkanols corresponding to R, or reactive esterified derivatives thereof such as alkyl halides, or diazoalkanes. Free acids are also converted into said metal, ammonium or acid addition salts in conventional manner.

Thus, any resulting free acid or base can be converted into a corresponding metal, ammonium or acid addition salt respectively, by reacting it with an equivalent amount of the corresponding base, basic salt, acid or ion exchange preparation, e.g. said free acids with alkali or ammonium hydroxides or carbonates, or e.g. free amines with said inorganic or organic acids respectively. Any resulting salt may also be converted into the free compound, by liberating the latter with stronger acids or bases, respectively. In view of the close relationship between the free compounds and the salts thereof, whenever a compound of the invention, or intermediate, is referred to in this context, a corresponding salt is also intended, provided such is possible or appropriate under the circumstances.

The compounds, including their salts, may also be obtained in the form of their hydrates, or include other solvents used for the crystallization. Furthermore, the functional derivatives of the free acids of formula I, wherein either the phosphono and/or carboxy groups are esterified by identical or different radicals may be prepared by condensing a free acid of formula I or a mono- or di-ester derivative thereof with an esterifying agent of the formula X

wherein Z represents hydroxy or a reactive esterified hydroxyl group; and $R_5$ represents an esterifying radical as defined herein for the phosphonyl esters (e.g. R and R') and the carboxylic esters (encompassed e.g. by $COR_3$ representing esterified carboxy), in particular said non-aromatic radicals.

A reactive esterified hydroxyl group, such as Z in a compound of the formula IX or X, is a hydroxyl group esterified by a strong inorganic or organic acid. Corresponding Z groups are in particular halo, for example chloro, bromo or preferably iodo, also sulfonyloxy groups, such as lower alkyl- or arylsulfonyloxy groups, for example (methane-, ethane-, benzene- or toluene-) sulfonyloxy groups, also the trifluoromethylsulfonyloxy group.

The esterification of the carboxyl or phosphonyl groups, optionally in salt form, with a compound of formula X wherein Z represents a reactive esterified hydroxyl group, is performed in a manner known per se, in the presence of for example an organic base, such as an organic amine, for example a tertiary amine, such as tri-lower alkylamine, for example trimethylamine, triethylamine or ethyl-di-isopropylamine, an N,N-di-lower-alkyl-aniline, for example N,N-di-methylaniline, a cyclic tertiary amine, such as an N-lower-alkylated morpholine, for example N-methyl-morpholine, a base of the pyridine type, for example pyridine, an inorganic base, for example hydroxides, carbonates, or hydrogen carbonates of alkali metals or alkaline-earth metals, for example sodium, potassium or calcium hydroxide, carbonate or hydrogen carbonate, or a quaternary ammonium base, such as a tetraalkylammonium hydroxide, carbonate or hydrogen carbonate, for example in which alkyl is e.g. methyl, ethyl, propyl, isopropyl, butyl, or the like, or an alkali metal salt of bis-trialkylsilylamide (e.g. trimethyl) optionally in the presence of a crown ether such as 18-crown-6 in a suitable inert solvent or solvent mixture, e.g. acetonitrile, toluene, and the like.

A trifunctional free acid, e.g. of the formula I, or a monoester or diester thereof, is preferably first converted into a salt of one of the stated organic or inorganic bases, especially into the sodium or potassium salt, and is then reacted with a compound of the formula X. The compounds of formula X are known or can be prepared by methods well-known to the art.

A compound of the formula or X wherein Z is a reactive esterified hydroxyl group can be prepared in situ. For example, a compound of the formula X wherein Z is chloro can be converted by treatment with sodium iodide in a solvent, for example in acetone or acetonitrile, into a compound of the formula X wherein Z is iodo; or esterification can be carried out with a chloro compound of the formula X in the presence of sodium iodide.

Esterification of a compound with a free carboxyl group using in excess an alcohol of formula X (wherein Z represents hydroxy) is carried out in a manner known per se, e.g. in the presence of an acid catalyst e.g. sulfuric acid or boron trifluoride etherate, preferably at an elevated temperature, advantageously ranging from about 40° C. to 100° C. Alternatively, the esterification of a compound with a free carboxyl group can be carried out with at least an equimolar amount of the alcohol in the presence of a condensing agent such as dicyclohexylcarbodiimide or N-(3-dimethylaminopropyl)-N'-ethylcarbodiimide in a polar solvent such as methylene chloride, in the presence of a base if required, e.g. such as 4-(dimethylamino)pyridine.

Conversely, esters of the invention, phosphonic acid or carboxylic acid esters, can be converted to compounds of the invention with a free carboxy and/or one or two free phosphonyl hydroxy groups using methods and conditions generally known in the art and illustrated herein. Depending on type of ester involved, useful reagents include aqueous acids or bases; also anhydrous reagents such as trialkylsilyl halides, hydrobromic acid in glacial acetic acid; also hydrogen and a hydrogenolysis catalyst. For instance, trialkyl esters can be converted to the free trifunctional acids by treatment with hydrobromic acid in glacial acetic acid, e.g. at room temperature or elevated temperature. Also trialkyl esters can be converted to the mono esters wherein carboxy only remains esterified, by treatment with e.g. trimethylsilyl bromide at room temperature.

Any benzyl esters can be selectively hydrogenolyzed with e.g. hydrogen in the presence of a catalyst such as palladium on charcoal.

Phosphono diesters wherein the esterifying groups (R and R') represent α-acyloxyalkyl (for instance the compounds of formula IIIa) can be converted to corresponding phosphono monoesters of formula IIIb (wherein one of R and R' represents hydrogen) by treatment with one molar equivalent of an aqueous base, e.g. 1N sodium hydroxide.

Phosphono diesters wherein the esterifying groups (e.g. R and R' in formula I or II) represent aryl (for instance the compounds of formula IIIc) can advantageously be converted to the corresponding phosphono monoesters (wherein one of R and R' represents hydrogen) using dilute aqueous acid (e.g. dilute hydrochloric acid) in a polar water miscible solvent such as acetonitrile.

Furthermore, phosphono diesters wherein the esterifying groups represent aryl can first be converted to the corresponding phosphono diesters wherein the esterifying groups represent e.g. methyl, by treatment with methanol in the presence of potassium fluoride and a crown ether such as 18-crown-6. Subsequent treatment with hydrobromic acid in glacial acetic acid yields the free phosphonic acid.

In the case mixtures of stereoisomers or optical isomers of the above compounds are obtained, these can be separated into the single isomers by methods in themselves known, e.g., by fractional distillation, crystallization and/or chromatography. Racemic products can be resolved into the optical antipodes, for example, by separation of diastereomeric salts thereof, e.g., for basic compounds by the fractional crystallization of d- or l-(tartrate, mandelate or camphorsulfonate) salts, or for acidic compounds by fractional crystallization of d- or l-(alpha-methylbenzylamine, cinchonidine, quinine, quinidine, ephedrine, dehydroabietylamine, brucine or strychnine)-salts.

The above-mentioned reactions are carried out according to standard methods, in the presence or absence of diluents, preferably such as are inert to the reagents and are solvents thereof, of catalysts, alkaline or acidic condensing or said other agents respectively and/or inert atmospheres, at low temperatures, room temperature or elevated temperatures, preferably near the boiling point of the solvents used, at atmospheric or superatmospheric pressure.

The invention further includes any variant of said processes, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being preferred.

The present invention additionally relates to the use in mammals of the compounds of the invention and their pharmaceutically acceptable, non-toxic acid addition salts, or pharmaceutical compositions thereof, as medicaments, e.g. as neutral endopeptidase inhibitors, e.g. for the treatment of cardiovascular disorders such as hypertension, edema, salt retention and congestive heart failure.

The present invention also relates to the use of the compounds of the invention for the preparation of pharmaceutical compositions especially pharmaceutical compositions having neutral endopeptidase inhibiting activity, and e.g. antihypertensive or saluretic activity.

The pharmaceutical compositions according to the invention are those suitable for enteral, such as oral or rectal, transdermal and parenteral administration to mammals, including man, for the treatment of cardiovascular disorders, such as hypertension, comprising an effective amount of a pharmacologically active compound of the invention or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salts and/or polyethyleneglycol; for tablets also c) binders, e.g. magnesium aluminum silicate, starch paste, gelatin, tragacanth, methylcellulose, sodium carboxymethylcellulose and/or polyvinylpyrrolidone; if desired, d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optically with carriers, optionally a rate controlling barrier to deliver the compound to the skin of the host at a controlled and predetermined rate over a prolonged period of time, and means to secure the device to the skin.

A unit dosage for a mammal of about 50 to 70 kg may contain between about 10 and 100 mg of the active ingredient. The dosage of active compound is dependent on the species of warm-blooded animal (mammal), the body weight, age and individual condition, and on the form of administration.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. Optical rotations are measured at room temperature at 589 nm (D line of sodium) or other wavelengths as specified in the examples.

The prefixes R and S are used to indicate the absolute configuration at each asymmetric center.

EXAMPLE 1

(S)-3-(Biphenyl-4-yl)-2-(dimethylphosphonomethylamino)-propionic acid (278 mg, 0.76 mmol) is dissolved in a 30% solution of hydrobromic acid in acetic acid (10 mL) under nitrogen. After 2 hours, ether (50 mL) is added and the product precipitates. The mixture is kept at 0° for 18 hours and then filtered. The solid is dissolved in 0.1N sodium hydroxide (25 mL) and the insoluble material is filtered. The filtrate is acidified with 2N hydrochloric acid (5 mL). The gelatinous solid is filtered, washed with water and dried under high vacuum at 75° to give the (S)-3-(biphenyl-4-yl)-2-(phosphonomethyl-amino)-propionic acid as a white powder; m.p.: 241° (dec.); $[\alpha]_D = +33.16$ (c 0.95, 0.1N NaOH).

The starting material is prepared as follows:

To a suspension of (S)-2-amino-3-(biphenyl-4-yl)-propionic acid methyl ester hydrochloride (J. Org. Chem., 1992, 57, 379; 10 g, 34.3 mmol) in water (200 mL) is added solid sodium bicarbonate (3.17 g, 37.7 mmol). The mixture is stirred for 30 minutes and then extracted with ether (3×80 mL). The combined organic phases are washed with brine (50 mL) and then dried over anhydrous magnesium sulfate. Evaporation of the solvent in vacuo affords (S)-2-amino-3-(biphenyl-4-yl)-propionic acid methyl ester as a white solid.

(S)-2-Amino-3-(biphenyl-4-yl)-propionic acid methyl ester (5 g, 19.6 mmol) is dissolved in methylene chloride (100 mL) at 0°. Diisopropyl ethylamine (3.74 mL, 21.5 mmol) is added, followed by a solution of dimethylphosphonomethyl trifluoromethylsulfonate (Tetrahedron Lett., 1986, 1477; 5.86 g, 21.5 mmol). The mixture is stirred for 2 hours, warmed to room temperature and stirred for 16 hours. The solution is washed with saturated sodium bicarbonate, water and brine. The organic layer is dried over anhydrous sodium sulfate, filtered and concentrated in vacuo. The residue is purified by flash-chromatography to afford an amber oil which solidifies upon standing, such being (S)-3-(biphenyl-4-yl)-2-[(dimethylphosphonomethyl)-amino]-propionic acid methyl ester, $[\alpha]_D= +1.16$ (c 0.77, MeOH).

(S)-3-(Biphenyl-4-yl)-2-[(dimethylphosphonomethyl)-amino]-propionic acid methyl ester (5 g, 13.2 mmol) is dissolved in methanol (60 mL) and cooled to 0°. 1N Sodium hydroxide (19.8 mL, 19.8 mmol) is added dropwise. The solution is stirred at room temperature for 4 hours, then neutralized with 1N hydrochloric acid (20.2 mL, 20.2 mmol). The solvent is removed in vacuo at 10° from the gelatinous solution. The residue is extracted with methylene chloride (3×20 mL). The combined organic layers are washed with brine, dried over anhydrous magnesium sulfate, filtered and concentrated in vacuo. The crude solid is triturated with acetonitrile, filtered and washed with ether. (S)-3-(Biphenyl-4-yl)-2-[(dimethylphosphonomethyl)-amino]-propionic acid is obtained as a white solid that is dried under vacuum at 60° for 16 hours, $[\alpha]_D= +77.34$ (c 0.83, MeOH).

EXAMPLE 2

According to the procedures in example 1, the following aminophosphonic acids can be prepared:
(1) (S)-3-(2-Methoxy-biphenyl-4-yl)-2-(phosphonomethylamino)-propionic acid, m.p.: 205°–208°, $[\alpha]_D= +5.99$ (c 0.61, 1N NaOH).
(2) (S)-3-(2'-Methoxy-biphenyl-4-yl)-2-(phosphonomethylamino)-propionic acid.

The starting material is prepared as follows:
To a cold (−78°) solution of n-butyllithium (2.5M in hexane, 5.1 mL, 12.8 mmol) in dry THF (20 mL) under nitrogen is added dropwise 2-bromoanisole (1.3 mL, 10.7 mmol). The mixture is stirred for 45 minutes, then treated with trimethylborate (3.64 mL, 32 mmol). The solution is allowed to warm up to room temperature and stirring is continued for 18 hours. A 0.5% HCl solution is added to reach pH 6.5. The product is extracted in methylene chloride (2×40 mL). The organic layer is dried over anhydrous sodium sulfate, filtered and concentrated in vacuo. The residue is triturated with hexane to give the boronic acid as a white solid (m.p. 102°). Palladium-catalyzed coupling to (S)-N-tBOC tyrosine O-trifluoromethanesulfonate methyl ester is carried out according to J. Org. Chem., 1992, 57, 379 to give (S)-2-t-butoxycarboxylamino-3-(2'-methoxy-biphenyl-4-yl)-propionic acid methyl ester.

Treatment with a 1:1 mixture of trifluoroacetic acid and methylene chloride for 1 hour at room temperature yields (S)-2-amino-3-(2'-methoxybiphenyl-4-yl)propionic acid methyl ester.
(3) (S)-3-(3-Methoxy-biphenyl-4-yl)-2-(phosphonomethylamino)-propionic acid.
(4) (S)-3-(3'-Methoxy-biphenyl-4-yl)-2-(phosphonomethylamino)-propionic acid.

EXAMPLE 3

(S)-4-(Biphenyl-4-yl)-3-[(dimethylphosphonomethyl)-amino]-butyric acid (321 mg, 0.85 mmol) is dissolved in a 30% solution of hydrobromic acid in acetic acid (5 mL) and stirred at room temperature for 18 hours. The reaction mixture is poured into cold water (20 mL) and the white precipitate is filtered off, then redissolved in 1N sodium hydroxide (20 mL). The resulting cloudy yellow solution is filtered, then acidified with 1N hydrochloric acid (25 mL). The white precipitate is washed with water (3×20 mL), filtered and dried under high vacuum. (S)-4-(Biphenyl-4-yl)-3-(phosphonomethylamino)-butyric acid hydrochloride is obtained as a white solid, m.p. 242°–244°, $[\alpha]_D= -8.79$ (c 0.72, 0.1N NaOH).

The starting material is prepared as follows:
Similarly to a method reported in J. Med. Chem., 1988, 31, 2199, to a stirred solution of (S)-2-t-butoxycarbonylamino-3-(biphenyl-4-yl)-propionic acid (J. Org. Chem., 1992, 57, 379; 1 g, 2.93 mmol) in THF (10 mL) at 0° is added N-methylmorpholine (0.35 mL, 3.18 mmol), followed by isobutyl chloroformate (0.39 mL, 3.0 mmol). The suspension is stirred for 1 hour, then filtered. The precipitate is washed with dry ether (5 mL). A saturated solution of diazomethane in ether is added at 0° until persistence of a yellow color. After stirring for 1 hour at 0° and 1 hour at room temperature, the solution is concentrated in vacuo to yeild the intermediate diazoketone as a beige solid (m.p. 128°–129°). The solid is suspended in methanol (10 mL). A solution of silver benzoate (150 mg, 0.65 mmol) in triethylamine (3 mL) is added dropwise. The dark solution is stirred at room temperature for 30 minutes, then filtered through Celite. The filtrate is concentrated under reduced pressure and the residue is redissolved in ethyl acetate (20 mL). The organic layer is washed successively with water (10 mL), saturated sodium bicarbonate (10 mL) and 1N hydrochloric acid (10 mL) before being dried over anhydrous sodium sulfate and filtered. After evaporation of the solvent in vacuo, the residue is purified by flash-chromatography on silica gel, eluting with 25% ethyl acetate in hexane. (S)-3-t-Butoxycarbonylamino-4-(biphenyl-4-yl)-butyric acid methyl ester is obtained as a solid, m.p. 86°–87°.

(S)-3-t-Butoxycarbonyl-amino-4-(biphenyl-4-yl)-butyric acid methyl ester (716 mg, 2 mmol) is stirred for 1 hour in a 1/1 mixture of trifluoroacetic acid and methylene chloride (5 mL). Ethyl acetate (20 mL) is added and the solution is washed with saturated sodium bicarbonate (20 mL). The organic layer is separated, dried over anhydrous sodium sulfate, filtered and concentrated in vacuo. The residue is dissolved in methylene chloride (10 mL) and cooled to 0° under nitrogen. Diisopropyl ethylamine (0.42 mL, 2.4 mmol) is added, followed by a solution of dimethylphosphonomethyl trifluoromethylsulfonate (Tetrahedron Lett., 1986, 1477; 545 mg, 2.2 mmol). The mixture is stirred for 18 hours at room temperature. The solution is washed with saturated sodium bicarbonate, water and brine. The organic layer is dried over anhydrous sodium sulfate, filtered and concentrated in vacuo. The residue is purified by flash-chromatography to afford (S)-4-(biphenyl-4-yl)-3-[(dimethylphosphonomethyl)-amino]-butyric acid methyl ester as a white solid, m.p. 67°.

To a solution of (S)-4-(biphenyl-4-yl)-3-[(dimethylphosphonomethyl)-amino]-butyric acid methyl ester (851 mg, 2.26 mmol) in methanol (2 mL) is added 2N sodium hydroxide (1.5 mL, 3 mmol). After 1 hour of stirring, methanol is removed under vacuum and water (5 mL) is added to the residue. The aqueous layer is washed with ethyl acetate (10 mL), then acidified with 1N hydrochloric acid (4 mL). The residue is extracted with ethyl acetate (2×10 mL) and methylene chloride (10 mL). The combined organic layers are dried over anhydrous sodium sulfate, filtered and concentrated in vacuo to yield (S)-4-(biphenyl-4-yl)-3-[(dimethylphosphonomethyl)-amino]-butyric acid as a gummy solid.

EXAMPLE 4

(1) (S)-5-(Biphenyl-4-yl)-4-[(dimethylphosphonomethyl)-amino]-2-pentenoic acid ethyl ester (536 mg, 1.28 mmol) is dissolved in methanol (1 mL) and treated with 1N sodium hydroxide (2 mL, 2 mmol). The reaction mixture is stirred for 3 hours at room temperature, then 1N hydrochloric acid (5 mL) is added. The carboxylic acid is extracted in methylene chloride (20 mL). The organic layer is separated, dried over anhydrous sodium sulfate, filtered and concentrated in vacuo. The residue is suspended in methylene chloride (2 mL) under nitrogen and treated with trimethylsilyl bromide (0.424 mL, 3.21 mmol). The clear solution is stirred at room temperature for 18 hours, then concentrated in vacuo. The residue is triturated with water (5 mL) and the precipitate is filtered off and then dissolved in 1N sodium hydroxide (5 mL). 1N Hydrochloric acid (8 mL) is added to precipitate the product which is filtered and washed with water (10 mL). The solid suspended in ethanol (5 mL) and stirred for 20 minutes with propylene oxide (2 mL). Concentration in vacuo yields (S)-5-(biphenyl-4-yl)-4-(phosphonomethylamino)-2-pentenoic acid as a white solid; m.p.: 231°–233°.

The starting material is prepared as follows:

Similarly to a method reported in Tetrahedron Lett., 1991, 923, to a stirred solution of (S)-2-t-butoxycarbonylamino-3-(biphenyl-4-yl)-propionic acid (3 g, 8.8 mmol) in dimethoxyethane (DME; 8 mL) at $-15°$ is added N-methyl morpholine (0.975 mL, 8.8 mmol), followed by isobutyl chloroformate (1.2 mL, 9.25 mmol). After 5 minutes, the precipitate is removed by filtration and washed with DME (5 mL). The filtrate is cooled to 0° and treated at once with a freshly prepared clear solution of sodium borohydride (500 mg) in water (5 mL). After the strong evolution of gas has ceased, water (100 mL) is added and the product is extracted in ethyl acetate. The organic layer is separated, dried over magnesium sulfate, decolorized with activated charcoal, filtered and concentrated in vacuo to yield (S)-2-t-butoxycarbonylamino-3-(biphenyl-4-yl)-propan-1-ol as a white solid, m.p.: 116°, $[\alpha]_D = -22.90$ (c 0.74, MeOH).

To a solution of oxalyl chloride (0.535 mL, 6.14 mmol) in methylene chloride (3 mL) cooled to $-70°$ under nitrogen is added dropwise dimethylsulfoxide (0.830 mL, 10.7 mmol) in methylene chloride (3 mL). After 20 minutes of stirring at $-70°$, a solution of (S)-2-t-butoxycarbonylamino-3-(biphenyl-4-yl)-propan-1-ol (1 g, 3.05 mmol) in methylene chloride (3 mL) is added, followed by triethylamine (2 mL, 14.3 mmol). The solution is allowed to warm up to room temperature over a 1 hour period, then poured into brine. Methylene chloride (50 mL) and water (80 mL) are added. The organic layer is separated, dried over anhydrous magnesium sulfate, filtered and concentrated in vacuo. The crude aldehyde is dissolved in methylene chloride (15 mL) and treated with (carboethoxymethylene)-triphenylphosphorane (2.1 g, 6.1 mmol). After stirring at room temperature for 18 hours, silica gel (2 g) is added and the solvent is evaporated under vacuum. The product is purified by flash-chromatography on silica gel, eluting with 25% ethyl acetate in hexane. (S)-4-(t-Butoxycarbonylamino)-5-(biphenyl-4-yl)-2-pentenoic acid ethyl ester is obtained as a white solid, m.p. 91°–94°.

(S)-4-t-Butoxycarbonylamino-5-(biphenyl-4-yl)-pentenoic acid ethyl ester (1.2 g, 3.03 mmol) is stirred for 1 hour in a 1/1 mixture of trifluoroacetic acid and methylene chloride (10 mL). A saturated aqueous solution of sodium bicarbonate (10 mL) is added and the product is extracted in methylene chloride (20 mL). The organic layer is dried over anhydrous sodium sulfate, filtered and cooled to 0° under nitrogen. To that solution is added N,N-diisopropylethylamine (0.633 mL, 3.63 mmol) in methylene chloride (2 mL), followed by a solution of dimethylphosphonomethyl trifluoromethylsulfonate (Tetrahedron Lett., 1986, 1477; 907 mg, 3.33 mmol) in methylene chloride (2 mL). The mixture is stirred at room temperature for 18 hours. Water (20 mL) and methylene chloride (20 mL) are added. The organic layer is separated, dried over anhydrous sodium sulfate, filtered and concentrated in vacuo. The residue is purified by flash-chromatography on silica gel, eluting with ethyl acetate to afford (S)-5-(biphenyl-4-yl)-4-[(dimethylphosphonomethyl)-amino]-2-pentenoic acid ethyl ester as a pale yellow oil (Rf=0.3 in EtOAc).

(2) Similarly prepared is (S)-5-(biphenyl-4-yl)-4-(phosphonomethylamino)-pentanoic acid, m.p.: 213°–215°, $[\alpha]_D = +2.87$ (c 0.64, 0.1N NaOH).

The starting (S)-5-(biphenyl-4-yl)-4-[(dimethylphosphonomethyl)-amino]-pentanoic acid is prepared from (S)-4-(t-butoxycarbonylamino)-5-(biphenyl-4-yl)-pentanoic acid ethyl ester. Such is in turn prepared as follows:

(S)-4-(t-Butoxycarbonylamino)-5-(biphenyl-4-yl)-pentenoic acid ethyl ester (1.6 g), is dissolved in ethanol and hydrogenated under 48 psi for 2 hours with Pd/C catalyst. The mixture is filtered through Celite and the filtrate is concentrated in vacuo to yield (S)-4-(t-butoxycarbonylamino)-5-(biphenyl-4-yl)-pentanoic acid ethyl ester.

EXAMPLE 5

(S)-3-(Biphenyl-4-yl)-2-[(diphenylphosphonomethyl)-amino]-propionic acid benzyl ester (0.8 g, 1.38 mmol) is dissolved in ethyl acetate (25 mL) and treated with hydrogen (50 lbs) in a Parr apparatus in the presence of 10% palladium on carbon (0.8 g). After uptake of 1 mole, the catalyst is filtered off and the solvent is evaporated in vacuo. The solid residue is recrystallized at 0° from ethyl acetate/hexane. After being dried under high vacuum at 50°, (S)-3-(biphenyl-4-yl)-2-[(diphenylphosphonomethyl)-amino]-propionic acid is obtained as a white solid, m.p. 118°–119°; $[\alpha]_{405} = +9.49$ (c 1.01, CHCl$_3$).

The starting material is prepared as follows:

(S)-2-(t-butoxycarbonylamino-3-(biphenyl-4-yl)-propionic acid methyl ester (4.1 g, 11.5 mmol) is dissolved at room temperature in methanolic 1N sodium hydroxide (60 mL). The solution is stirred for 3 hours. Ether (30 mL) and water (30 mL) are added. The aqueous layer is separated and acidified with concentrated hydrochloric acid, then extracted with ether (2×20 mL) and dried over anhydrous sodium sulfate. Evaporation of the solvent under reduced pressure gives (S)-2-(t-butoxycarbonylamino)-3-(biphenyl-4-yl)-propionic acid as a white solid, m.p. 122°–123°.

(S)-2-(t-Butoxycarbonylamino)-3-(biphenyl-4-yl)propionic acid (5 g, 14.6 mmol) is dissolved in methylene chloride (25 mL) under nitrogen and the solution is cooled to 0°. Benzyl alcohol (2 mL, 19 mmol) and 4-dimethylaminopyridine (0.1 g) are added, followed by a solution of dicyclohexyl-carbodiimide (3.3 g, 16.1 mmol) in methylene chloride (15 mL). After stirring for 1 hours at 0° and 1 hours at room temperature, the reaction mixture is filtered and the filtrate concentrated in vacuo. The residue is redissolved in ether (100 mL), washed successively with water, 0.5M sodium dihydrogenophosphate, water, saturated sodium bicarbonate and water. The organic layer is dried over anhydrous sodium sulfate, filtered and concentrated under reduced pressure. (S)-2-(t-butoxycarbonylamino)-3-(biphenyl-4-yl)-propionic acid benzyl ester is obtained as a white solid, $[\alpha]_D = -3.33$ (c 0.91, CHCl$_3$).

A stirred solution of (S)-2-(t-butoxycarbonylamino)-3-(biphenyl-4-yl)-propionic acid benzyl ester (3.95 g, 9.15 mmol) in ethyl acetate (40 mL) under nitrogen is cooled to 0° and treated with hydrochloric acid gas (4 g). A precipitate appears and the mixture is warmed to room temperature and stirred for 1 hour. Ether (25 mL) is added and the solid is filtered off and briefly dried under high vacuum for 1 hour. (S)-2-amino-3-(biphenyl-4-yl)-propionic acid benzyl ester hydrochloride is obtained as white solid, $[\alpha]_D = -21.14$ (c 0.92, MeOH).

To a stirred mixture of (S)-2-amino-3-(biphenyl-4-yl)-propionic acid benzyl ester hydrochloride (4.7 g, 12.8 mmol) in ethyl acetate (100 mL) and water (100 mL) at 5° is added sodium bicarbonate (1.13 g, 13.5 mmol). The solution is stirred for 5 minutes, then aqueous formaldehyde (37% aq., 1.25 mL, 16.6 mmol) is added. The mixture is allowed to warm slowly to room temperature while being stirred vigorously for 18 hours. The organic layer is separated and the aqueous layer extracted with ethyl acetate (50 mL). The combined organic phases are washed with water (50 mL), dried over anhydrous sodium sulfate, filtered and concentrated in vacuo. The resulting crude hexahydrotriazine intermediate is obtained as a white solid that is dried under high vacuum. Some of that material (0.75 g, 2.18 mmol) is dissolved in toluene (10 mL) and kept under nitrogen. Diphenyl phosphite (0.5 mL, 2.62 mmol) is added and the solution is warmed in a bath pre-heated to 70°. After 2 hours, the reaction mixture is allowed to cool to room temperature. After evaporation of the solvent under reduced pressure, the residue is purified by flash-chromatography on silica gel, eluting with a gradient of ethyl acetate (50% to 90%) in hexane. The product is recrystallized from ether/hexane, affording (S)-3-(biphenyl-4-yl)-2-[(diphenylphosphonomethyl)-amino]-propionic acid benzyl ester as a while solid, m.p. 85°-86°; $[\alpha]_D = +8.40$ (c 1.04, CHCl$_3$).

EXAMPLE 6

The following compounds are prepared using procedures similar to Example 5. (1) (S)-3-(Biphenyl-4-yl)-2-{[di-(3-methyl-phenyl)-phosphonomethyl]-amino}-propionic acid, m.p. 74°-76°; $[\alpha]_D = -3.15$ (c 0.97, CHCl$_3$).

The starting di-(3-methylphenyl) phosphite is prepared as follows:

To a stirred solution of m-cresol (5.1 g, 47 mmol) in methylene chloride (5 mL) cooled to 0° under nitrogen is added methanol (0.97 mL, 24 mmol). Phosphorus trichloride (2 mL, 23 mmol) is then added dropwise over 20 minutes. The flask is vented to allow the hydrochloric acid formed to escape, then the mixture is allowed to warm up slowly to room temperature and stirred for 10 hours. The solvent is removed under reduced pressure and the residue is dried under high vacuum. Di-(3-methylphenyl)phosphite is characterized by H$^1$-NMR in CDCl$_3$ (P-H: 7.27 ppm, J=727.5 Hz) and used without further purification.

The diaryl phosphite starting materials for the compounds listed below are similarly prepared from the appropriate phenol.

(2) (S)-3-(Biphenyl-4-yl)-2-{[di-(3,5-dimethyl-phenyl)-phosphonomethyl]-amino}-propionic acid, m.p. 76°-78°; $[\alpha]_D = +2.48$ (c 0.99, CHCl$_3$).

(3) (S)-3-(Biphenyl-4-yl)-2-{[di-(3-methoxyphenyl)-phosphonomethyl]-amino}-propionic acid.

(4) (S)-3-(Biphenyl-4-yl)-2-{[di-4-acetylaminophenyl)-phosphonomethyl]-amino}-propionic acid.

(5) (S)-3-(2-Methoxy-biphenyl-4-yl)-2-[(diphenylphosphonomethyl)-amino]-propionic acid.

(6) (S)-3-(2'-Methoxy-biphenyl-4-yl)-2-[(diphenylphosphonomethyl)-amino]-propionic acid.

(7) (S)-3-(3-Methoxy-biphenyl-4-yl)-2-[(diphenylphosphonomethyl)-amino]-propionic acid.

(8) (S)-3-(3'-Methoxy-biphenyl-4-yl)-2-[(diphenylphosphonomethyl)-amino]-propionic acid.

(9) (S)-4-(Biphenyl-4-yl)-3-[(diphenylphosphonomethyl)-amino]-butyric acid.

(10) (S)-5-(Biphenyl-4-yl)-4-[(diphenylphosphonomethyl)-amino]-pentanoic acid.

(11) (S)-5-Biphenyl-4-yl)-4-[diphenylphosphonomethyl)-amino]-pentanoic acid.

EXAMPLE 7

To a stirred solution of (S)-3-(biphenyl-4-yl)-2-[(diphenyl-phosphonomethyl)-amino]-propionic acid in THF is added 2N hydrochloric acid. The mixture is stirred at room temperature for 18 hours. Ethyl acetate and water are added. The organic phase is separated and washed successively with 1N hydrochloric acid, water and brine. After filtration, the organic layer is concentrated and the residue is purified by flash-chromatography on silica gel, eluting with 4% of methanol in methylene chloride to yield (S)-3-(biphenyl-4-yl)-2-{[(monophenyl-phosphonomethyl)-amino]-propionic acid.

EXAMPLE 8

The following compounds are prepared similarly to procedure in Example 7.

(1) (S)-3-(biphenyl-4-yl)-2-{[mono-(3,5-dimethyl-phenyl)-phosphonomethyl]-amino}-propionic acid.

(2) (S)-3-(Biphenyl-4-yl)-2-{[mono-(3-methylphenyl)-phosphonomethyl]-amino}-propionic acid.

(3) (S)-3-(Biphenyl-4-yl)-2-{[mono-(3-methoxyphenyl)-phosphonomethyl]-amino}-propionic acid.

(4) (S)-3-(Biphenyl-4-yl)-2-{[mono-(4-acetylaminophenyl)-phosphonomethyl]-amino}-propionic acid.

(5) (S)-3-(2-Methoxy-biphenyl-4-yl)-2-[(mono-phenyl-phosphonomethyl)-amino]-propionic acid.

(6) (S)-3-(2'-Methoxy-biphenyl-4-yl)-2-[(mono-phenyl-phosphonomethyl)-amino]-propionic acid.

(7) (S)-3-(3-Methoxy-biphenyl-4-yl)-2-[(mono-phenyl-phosphonomethyl)-amino]-propionic acid.

(8) (S)-3-(3'-Methoxy-biphenyl-4-yl)-2-[(mono-phenyl-phosphonomethyl)-amino]-propionic acid.

EXAMPLE 9

(S)-3-Biphenyl-4-yl-2-{[di-(ethoxycarbonylmethyl)-phosphonomethyl]-amino}-propionic acid benzyl ester (0.18 g, 0.3 mmol) is dissolved in ethyl acetate (12 mL) and hydrogenated at 50 lbs pressure in a Parr apparatus in the presence of 10% palladium on carbon (0.1 g). After 6 hours, the reaction mixture is filtered and concentrated in vacuo. The resulting gummy solid is recrystallized from ether-hexane at 0°. (S)-3-(biphenyl-4-yl)-2-{[di-(ethoxycarbonylmethyl)-phosphonomethyl]-amino}-propionic acid after being dried under high vacuum at 45°, is obtained as a crystalline solid, m.p. 85°-87°.

The starting material is prepared as follows:

To a stirred solution of ethyl glycolate (7.2 g, 69 mmol) in cold (ice bath) methylene chloride (8 mL) is added dropwise phosphorus trichloride (2 mL, 23 mmol). The solution is stirred at room temperature for 16 hours. The solution is concentrated under high vacuum and the obtained crude di-(ethoxycarbonylmethyl)phosphite is used directly.

Alternately, di-(ethoxycarbonylmethyl)phosphite can be prepared as follows:

To a stirred solution of dry phosphorous acid (1 g, 12.2 mmol) in anhydrous acetonitrile (10 mL) under nitrogen, is added, at 0°, diisopropylethylamine (4.25 mL), followed by ethyl bromoacetate (2.72 mL, 24.4 mmol). The mixture is allowed to warm slowly to room temperature and stirred for 18 hours. The solvent is removed under reduced pressure and the residue taken up in ethyl acetate. The solid material is filtered off and the filtrate is washed successively with cold 1N hydrochloric acid and water. The organic layer is dried over anhydrous magnesium sulfate, filtered and concentrated in vacuo. The residue is dried under high vacuum, yielding di-(ethoxycarbonylmethyl) phosphite as an amber oil characterized by H$^1$-NMR in CDCl$_3$ (P-H: 7.23 ppm, J=625 Hz).

The hexahydro-triazine intermediate described in example 5 (0.28 g, 0.82 mmol) is dissolved in toluene (3.5 mL) under nitrogen and treated with di-(ethoxycarbonylmethyl) phosphite (0.41 g, 1.61 mmol). The solution is heated to 70° for 4 hours. Ethyl acetate (10 mL) is added at room temperature and the organic layer is washed successively with water, 1N hydrochloric acid and water before being dried over anhydrous sodium sulfate, filtered and concentrated in vacuo. The residue is purified by flash-chromatography on silica gel, eluting with a gradient of ethyl acetate (35% to 50%) in hexane to give (S)-3-(biphenyl-4-yl)-2-{[di-(ethoxycarbonylmethyl)-phosphonomethyl]-amino}-propionic acid benzyl ester as an oil (MS: M+1=598).

EXAMPLE 10

The following compounds are prepared using procedure similar to Example 9.

(1) (S)-3-(Biphenyl-4-yl)-2-{[di-(isopropyloxycarbonylmethyl)-phosphonomethyl]-amino}propionic acid.
(2) (S)-3-(Biphenyl-4-yl)-2-{[di-(dimethylcarbamoylmethyl)-phosphonomethyl]-amino}-propionic acid.
(3) (S)-3-(Biphenyl-4-yl)-2-{[di-(2,2,2-trichloroethyl)-phosphonomethyl]-amino}-propionic acid.
(4) (S)-3-(2-Methoxy-biphenyl-4-yl)-2-{[di-(ethoxycarbonylmethyl)-phosphonomethyl]-amino}-propionic acid.
(5) (S)-3-(2'-Methoxy-biphenyl-4-yl)-2-{[di-(ethoxycarbonylmethyl)-phosphonomethyl]-amino}-propionic acid.
(6) (S)-3-(3-Methoxy-biphenyl-4-yl)-2-{[di-(ethoxycarbonylmethyl)-phosphonomethyl]-amino}-propionic acid.
(7) (S)-3-(3'-Methoxy-biphenyl-4-yl)-2-{[di-(ethoxycarbonylmethyl)-phosphonomethyl]-amino}-propionic acid.
(8) (S)-4-(Biphenyl-4-yl)-3-{[di-(ethoxycarbonylmethyl)-phosphonomethyl]-amino}-butyric acid.
(9) (S)-5-(Biphenyl-4-yl)-4-{[di-(ethoxycarbonylmethyl)-phosphonomethyl]-amino}-pentanoic acid.

EXAMPLE 11

Preparation of 1,000 capsules each containing 50 mg of the active ingredient, as follows:

| | |
|---|---|
| (S)-3-(Biphenyl-4-yl)-2-[(diphenylphosphonomethyl)-amino]-propionic acid | 50.00 g |
| Lactose | 167.00 g |
| Modified starch | 80.00 g |
| Magnesium stearate | 3.00 g |

Procedure: All the powders are passed through a screen with openings of 0.6 mm. The drug substance is placed in a suitable mixer and mixed first with the magnesium stearate, then with the lactose and starch until homogenous. No. 2 hard gelatin capsules are filled with 300 mg of said mixture each, using a capsule filling machine.

Analogously capsules are prepared, containing about 10-100 of the other compounds disclosed and exemplified herein.

What is claimed is:

1. A compound of the formula I

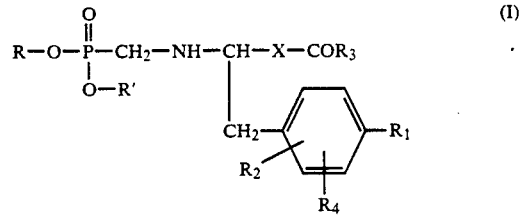

wherein X represents a direct bond, C$_{1-4}$-alkylene or C$_2$-C$_4$-alkenylene; R and R' represent independently hydrogen, carbocyclic aryl, 6-tetrahydronaphthyl, 5-indanyl, α-(trichloromethyl, carboxyl, esterified carboxyl or amidated carboxyl)substituted-(lower alkyl or aryl-lower alkyl), acyloxymethyl optionally monosubstituted on methyl carbon by C$_{1-20}$-alkyl, by C$_5$-C$_7$-cycloalkyl, by aryl or by aryl-lower alkyl; R$_1$ represents monocyclic carbocyclic or monocyclic heterocyclic aryl; COR$_3$ represents carboxyl or carboxyl derivatized in form of a pharmaceutically acceptable ester; R$_2$ and R$_4$ represent hydrogen, lower alkyl, trifluoromethyl, lower alkoxy or halogen; or a pharmaceutically acceptable salt thereof.

2. A compound according to claim 1 of formula I wherein X represents a direct bond, C$_{1-4}$-alkylene or C$_2$-C$_4$-alkenylene; R and R' independently represent hydrogen, carbocyclic aryl, α-(trichloromethyl, carboxyl, esterified carboxyl or amidated carboxyl) substituted-(lower alkyl or aryl-lower alkyl), (carbocyclic aroyloxy or C$_1$-C$_{20}$-alkanoyloxy)methyl optionally substituted on the methyl carbon by lower alkyl, by C$_5$, C$_6$ or C$_7$-cycloalkyl or by carbocyclic aryl; R$_1$ represents phenyl or phenyl mono- or disubstituted by lower alkyl, lower alkoxy, halogen or trifluoromethyl; or R$_1$ represents pyridyl, thienyl or furanyl, each optionally substituted by lower alkyl; R$_2$ represents hydrogen; COR$_3$ represents carboxyl or carboxyl derivatized in form of a pharmaceutically acceptable prodrug ester; R$_4$ represents hydrogen, lower alkyl, lower alkoxy, halogen or trifluoromethyl; or a pharmaceutically acceptable salt thereof.

3. A compound according to claim 2 of formula I wherein R and R' independently represent hydrogen, 5-indanyl, phenyl, or phenyl substituted by one, two or three substituents selected from lower alkyl, halogen, lower alkoxy, lower alkanoylamino, trifluoromethyl, lower alkyl-(thio, sufinyl or sulfonyl) and lower alkoxycarbonyl; or a pharmaceutically acceptable salt thereof.

4. A compound according to claim 2 of the formula I wherein R and R' independently represent hydrogen or α-(carboxy, lower alkoxycarbonyl, carbocyclic arylmethoxycarbonyl, aminocarbonyl, mono- or di-lower alkylaminocarbonyl or trichloromethyl) substituted-(lower alkyl or carbocyclic aryl-lower alkyl); or a pharmaceutically acceptable salt thereof.

5. A compound according to claim 2 of the formula I wherein COR$_3$ represents carboxyl, lower alkoxycarbonyl, (carbocyclic or heterocyclic aryl)-lower alkoxycarbonyl, (di-lower alkylamino, N-lower alkylpiperazino, morpholino, pyrrolidino, piperidino or perhydrazepino)-C$_2$ to C$_4$-alkoxycarbonyl, dihydroxypropyloxycarbonyl protected in form of a ketal, 5-indanyloxycarbonyl, α-(lower alkoxycarbonyl or di-lower alkylaminocarbonyl)-lower alkoxycarbonyl or 1-(lower alkanoyloxy)-lower alkoxycarbonyl; or a pharmaceutically acceptable salt thereof.

6. A compound according to claim 2 wherein COR$_3$ represents carboxyl; or a pharmaceutically acceptable salt thereof.

7. A compound according to claim 2 wherein X represents a direct bond; or a pharmaceutically acceptable salt thereof.

8. A compound according to claim 1 of the formula

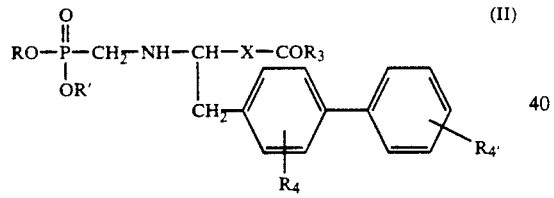

(II)

wherein X represents a direct bond, C$_{1-2}$-alkylene or C$_2$-alkenylene; R and R' independently represent hydrogen, carbocyclic aryl, 5-indanyl, α-(carboxyl, lower alkoxycarbonyl, carbocyclic arylmethoxycarbonyl, aminocarbonyl or mono- or di-lower alkylaminocarbonyl or trichloromethyl) substituted-(lower alkyl or carbocyclic aryl-lower alkyl), or

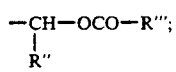

R'' represents hydrogen, C$_1$-C$_{20}$-alkyl, C$_5$, C$_6$ or C$_7$-cycloalkyl or carbocyclic aryl; R''' represents C$_1$-C$_{20}$-alkyl, C$_5$, C$_6$ or C$_7$-cycloalkyl, carbocyclic aryl or carbocyclic aryl-lower alkyl; COR$_3$ represents carboxyl, C$_1$-C$_{20}$-alkoxycarbonyl, (carbocyclic or heterocyclic aryl)-lower alkoxycarbonyl, (di-lower alkylamino, N-lower alkylpiperazino, morpholino, pyrrolidino, piperidino or perhydrazepino)-C$_2$ to C$_4$-alkoxycarbonyl, dihydroxypropyloxycarbonyl protected in form of a ketal, 5-indanyloxycarbonyl, α-(lower alkoxycarbonyl or di-lower alkylaminocarbonyl)-lower alkoxycarbonyl; R$_4$ and R$_4$' represent hydrogen, lower alkyl, lower alkoxy, halogen or trifluoromethyl; or a pharmaceutically acceptable salt thereof.

9. A compound according to claim 8 wherein COR$_3$ represents carboxyl; or a pharmaceutically acceptable salt thereof.

10. A compound according to claim 1 of the formula III

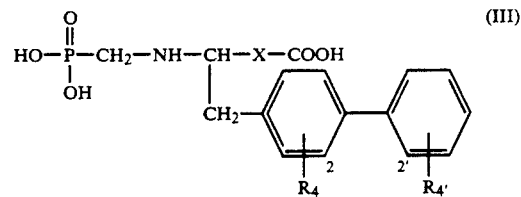

wherein X represents a direct bond, methylene or ethenylene; R$_4$ and R$_4$' represent hydrogen or C$_1$-C$_3$alkoxy; and pharmaceutically acceptable mono-, di- or tri-ester derivatives thereof in which one, two or three of the acidic hydroxy groups of the carboxyl and phosphono functional groups are esterified in form of a mono-, di- or tri-pharmaceutically acceptable prodrug ester; or a pharmaceutically acceptable salt thereof; or an optical or stereoisomer thereof.

11. A compound according to claim 1 of the formula

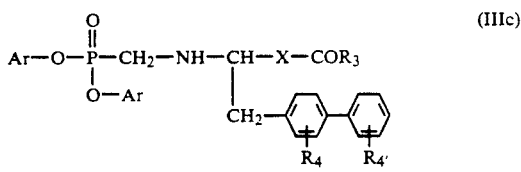

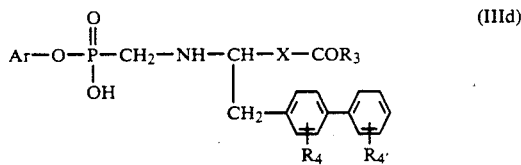

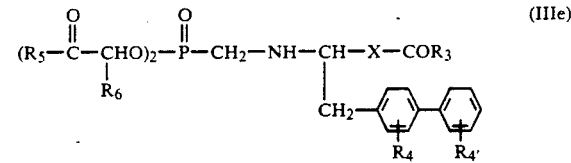

or

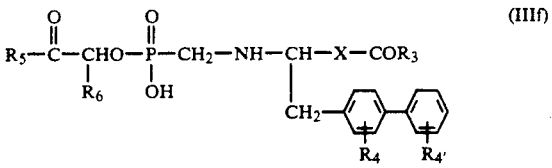

wherein X represents a direct bond, methylene or ethenylene; Ar represents phenyl or phenyl substituted by lower alkyl, lower alkoxy, halogen, trifluoromethyl, lower alkanoylamino, lower alkyl-(thio, sulfinyl or sulfonyl) or lower alkoxycarbonyl; or Ar represents 5-indanyl; R$_5$ represents hydroxy, lower alkoxy, aryl-lower alkoxy or di-lower alkylamino; R$_6$ represents hydrogen or lower alkyl; COR$_3$ represents carboxyl; or COR$_3$ represents carboxyl esterified in form of a pharmaceutically acceptable prodrug ester preferably selected from $C_1$–$C_{20}$-alkoxycarbonyl, (carbocyclic or heterocyclic aryl)-methoxycarbonyl, (di-lower alkylamino)-$C_2$ to $C_4$-alkoxycarbonyl, dihydroxypropyloxycarbonyl protected in form of a ketal, (lower alkoxycarbonyl or di-lower alkylaminocarbonyl)-methoxycarbonyl, 5-indanyloxycarbonyl, 1-(lower alkanoyloxy)-lower alkoxycarbonyl; $R_4$ and $R_4{}'$ represent hydrogen or $C_1$–$C_3$alkoxy; or a pharmaceutically acceptable salt thereof.

12. A compound according to claim 10 which is (S)-3-(biphenyl-4-yl)-2-(phosphonomethyl-amino)-propionic acid or a pharmaceutically acceptable salt thereof.

13. A compound according to claim 10 which is (S)-3-(2-methoxy-biphenyl-4-yl)-2-(phosphonomethylamino)-propionic acid or a pharmaceutically acceptable salt thereof.

14. A compound according to claim 10 which is (S)-4-(biphenyl-4-yl)-3-phosphonomethylamino)-butyric acid or a pharmaceutically acceptable salt thereof.

15. A compound according to claim 10 which is (S)-3-(biphenyl-4-yl)-2-[(diphenylphosphonomethyl)-amino]-propionic acid or a pharmaceutically acceptable salt thereof.

16. A compound according to claim 10 which is (S)-3-(biphenyl-4-yl)-2-{[di(ethoxycarbonylmethyl)phosphonomethyl]-amino}-propionic acid or a pharmaceutically acceptable salt thereof.

17. A neutral endopeptidase inhibiting pharmaceutical composition comprising an effective neutral endopeptidase inhibiting amount of a compound of claim 1 in combination with one or more pharmaceutically acceptable carriers.

18. A method of treating cardiovascular disorders in mammals which comprises administering to a mammal in need thereof an effective neutral endopeptidase inhibiting amount of a compound of claim 1.

19. A method of treating cardiovascular disorders in mammals which comprises administering to a mammal in need thereof an effective neutral endopeptidase inhibiting amount of a compound of claim 10.

* * * * *